United States Patent
Beška et al.

(12) 
(10) Patent No.: US 6,388,136 B1
(45) Date of Patent: May 14, 2002

(54) METHOD OF PREPARATION OF 4-AMINODIPHENYLAMINE

(75) Inventors: Emanuel Beška; Peter Toman, both of Bratislava; Karol Fiedler, Dunajská Lužná ; Milan Hronec, Bratislava; Jozef Pintèr, Nitra, all of (SK)

(73) Assignee: Duslo, A.S. Sala, Sala (SK)

( * ) Notice: Subject to any disclaimer, the term of this patent is extended or adjusted under 35 U.S.C. 154(b) by 0 days.

(21) Appl. No.: 09/875,881

(22) Filed: Jun. 8, 2001

Related U.S. Application Data

(63) Continuation of application No. PCT/SK99/00010, filed on Apr. 29, 1999.

(51) Int. Cl.[7] .............................................. C07C 209/00
(52) U.S. Cl. ...................................................... 564/420
(58) Field of Search ......................................... 564/420

(56) References Cited

U.S. PATENT DOCUMENTS

| | | |
|---|---|---|
| 5,117,063 A | 5/1992 | Stern et al. |
| 5,252,737 A | 10/1993 | Stern et al. |
| 5,739,403 A | 4/1998 | Reinartz et al. |

FOREIGN PATENT DOCUMENTS

| | | | |
|---|---|---|---|
| EP | 0 784 049 A | | 7/1997 |
| GB | 713622 A | | 8/1954 |
| WO | 0035853 | * | 6/2000 |

OTHER PUBLICATIONS

Aryeh A. Frimer, et al.; "Reaction of (Arylmethyl)amines with Superoxide Anion Radical in Aprotic Media. Insights into Cytokinin Senescence Inhibition", *J. Org. Chem.* vol. 48, pp. 1700–1705 (1982).

A. Wohl: Zur Kenntniss de Reaction zwischen Nitrobenzol und Anilin Bei Gegenwart von Alkali; *Mittheilung aus dem I. Berliner Universitats–Laboratorium* (1903) pp. 4135–4138.

M. K. Stern et al.; "Eliminating Chlorine in the synthesis of aromatic amines; new routes which utilize nucleophilic aromatic substitution for hydrogen" *New J. Chem.*, 1996, vol. 20, pp. 259–268.

* cited by examiner

*Primary Examiner*—Samuel Barts
(74) *Attorney, Agent, or Firm*—Pennie & Edmonds LLP

(57) ABSTRACT

A method of preparing 4-aminodiphylamine through an intermediate preparation of 4-nitrodiphenylamine and/or 4-nitrosodiphenylamine and/or their salts by reaction of aniline with nitobenzene in a liquid medium at a temperature of 50 to 130° C., under normal or reduced pressure, in an inert atmosphere or in the presence of air oxygen, with subsequent hydrogenation of an intermediate of 4-nitrodiphenylamine and/or nitrosodiphenylamine and side products, and by isolation of 4-aminodiphenylamine and the side products of unconverted raw materials.

16 Claims, No Drawings

METHOD OF PREPARATION OF 4-AMINODIPHENYLAMINE

RELATED APPLICATIONS

This is a continuation of the U.S. National Stage Designation of PCT/SK99/00010, filed Apr. 29, 1999.

TECHNICAL FIELD

Present invention relates to a method of preparation of 4-aminodiphenylamine (4-ADFA) through an intermediary preparation of 4-nitrodiphenylamine and/or 4-nitrosodiphenylamine and/or their salts in which aniline reacts with nitrobenzene in a liquid medium, whereby precursors of 4-ADFA are formed, i.e. 4-nitrosodiphenylamine (4-NODFA), 4-nitrodiphenylamine (4-$NO_2$DFA) an/or their salts which, after hydrogenation, result in 4-ADFA.

BACKGROUND ART 4-aminodiphenylamine (4-ADFA) is widely used as an intermediate product in the production of alkylated derivatives having outstanding properties as antiozonants, antioxidants and stabilizers.

Present methods of industrial production of 4-ADFA start with hydrogenation of the intermediates, 4-NODFA or 4-$NO_2$DFA. However, production of these intermediates, consisting in several technologically demanding steps, is accompanied by a number of side products, organic and inorganic waste which must be liquidated, this being one of the greatest problems of this production method.

Alternative methods of preparation of 4-ADFA intermediates which are ecologically and economically preferred consist in the direct reaction of aniline with nitrobenzene. The reaction is initiated by bases which form an anilide anion through the reaction which anion subsequently substitutes hydrogen in nitrobenzene by nucleophilic addition [A. Wohl et al., Ber. 34, 2442–2450, 1901; and A. Wohl, Ber. 36, 4135–4138, 1903], wherein if solid potassium hydroxide has been used as the base, mostly phenazine and phenazine oxide result, if sodium hydroxide has been used, also 4-NODFA is obtained.

In fifties, a number of authors have studied and described mechanism of the Wohl-Aue nucleophilic reaction of aniline and its derivatives with aromatic nitrocompounds by the action of bases (NaOH, KOH, eventually Na$NH_2$) in the medium of benzene, toluene and xylene, wherein phenazine derivatives are formed. Besides them also further reaction products like 4-nitrosodiphenylamine, 4-nitrosubstituted diphenylamines, azobenzenes, azoxybenzenes [E. I. Abramova et al., Zhur. Obshchei Khim. 22, 502–509, 1953; S. B. Serebryanyi, Uspekhi Khimii 24, 313–345, 1955; S. B. Serebryanyi, Ukrain. Khim. Zhur. 21, 350–360, 1955; V. P. Chemetskii et al., Zhur. Obshchei Khim. 25, 2161–2170, 1955] have been isolated and decribed at the same time.

It is known [N. R. Ayyangar et al., Tetrahedron Letters 31, 3217–3220, 1990] that 4-NODFA and 4-$NO_2$DFA arise by the reaction of nitrobenzene with acetanilide in the presence of dipolar aprotic solvent, dimethyl sulfoxide (DMSO), by the action of sodium hydroxide and potassium carbonate, as well as [A. A. Frimer et al., J. Org. Chem. 48, 1700–1705, 1983] that 4-$NO_2$DFA arises with a yield of up to 24% by the reaction of aniline with nitrobenzene in the presence of bases, in this case of potassium butoxide or potassium peroxide in the medium of benzene and in the presence of a crown ether.

Similarly [D. J. Stuehr et al., J. Org. Chem. 50, 694–696, 1985], by the reaction of aniline and N-methylaniline in DMSO with potassium peroxide, together with 18-crown-6-ether, as well as with tertiary potassium butoxide a mixture of 4-NODFA, 4-$NO_2$DFA, 4-ADFA, azobenzene, 4-phenylazodiphenylamine and phenylformamide has been obtained as the reaction product (no yields given).

Preparation of 4-ADFA through oxidation of aniline by ferricyanide in strongly alkaline medium is known [U.S. Pat. No. 4,760,186 and GB patent 1 440 767], wherein head-foot linking of two aniline molecules comes into effect, but with a low yield only.

U.S. Pat. No. 5,574,187 describes the 4-ADFA preparation by substitution of phenylhydroxylamine by aniline in the presence of an acidic catalyst. The product has been obtained with average yields only (max. of 51.2%).

Nature of the next U.S. Pat. No. 5,420,354 consists in the reaction of nitrobenzene with aniline in the presence of hydrogen, hydrogenation catalyst, acidic catalyst and hydrogenation inhibitor, which reaction yields directly 4-ADFA, but with relatively low yields (max. of 12%) and at a low selectivity of the reaction, similarly to other above given procedures.

In the EP application 566 783, the AKZO N.V. describes a method of manufacture of 4-nitrodiphenylamine by the reaction of nitrobenzene with aniline in the medium of a polar aprotic solvent, particularly dimethyl sulfoxide and tertiary butanol in a strongly alkaline reaction system, wherein hydroxides of alkali metals and of alkaline-earth metals, alkoxides, amides and hydrides of alkali metals have been used as bases, eventually in the presence of a phase transfer catalyst, like tetrabutylammonium hydrogen sulfate. Relatively high yields have been achieved, but selectivity of the reaction is insufficient. Therefore, it is necessary to isolate the product (NO$_2$DFA) from the side products by crystallization. Moreover, in the process of products isolation salts are obtained, thus causing further costs for their processing. Also lossless recycling of bases and solvent mixtures back to the process is questionable.

A further halogen free method of 4-ADFA preparation consists in the reaction of aniline with 4-phenylazodiphenylamine in the presence of strong bases, like tertiary potassium butoxide with crown ethers or with quaternary ammonium hydroxides [U.S. Pat. Nos. 5,382, 691, 5,633,407, 5,618,979 and 5,451, 702]. Subsequent transformation of 4-FADFA to 4-ADFA can be performed either by a catalytic hydrogenation according to the U.S. Pat. No. 5,451,702] or by a nucleophilic substitution reaction of 4-FADFA with amine in the presence of strong bases [U.S. Pat. Nos. 5,382,691, 5,633,407 and 5,618,979]. 4-ADFA can be also [see the U.S. Pat. Nos. 5,618,979 and 5,633,407 and the paper M. K. Stern et al., J. Org. Chem. 59, 5627–5632, 1994] prepared in one step directly by the reaction of azobenzene, eventually azoxybenzene, with aniline in the presence of strongly alkaline catalysts. However, in all above given procedures the starting raw material is azobenzene which is technically less easily accessible raw material, and it must be prepared in advance. Moreover, much waste arises which must be necessarily further treated or liquidated.

In a number of patents of the firm Monsanto [U.S. Pat. Nos. 5,117,063, 5,453,541, 5,608,111, 5,623,088], there is described a method of 4-ADFA intermediates production by direct reaction of aniline with nitrobenzene in an aprotic solvent with a controlled amount of a protic solvent by the action of bases, which include alkali hydroxides, alkoxides, hydrides and quaternary ammonium hydroxides with alkyl-, aryl- and aralkylsubstituents, as well as alkylsubstituted diammonium hydroxides. Nevertheless, the reaction products could be obtained with high yields and with high selectivity only when using quaternary ammonium hydroxides. Also mechanism of the reaction is known [M. K. Stern et al., J. Am. Chem. Soc. 114, 9237–9238, 1992, and New J. Chem. 20, 259–268, 1996].

From a comparison of the respective bases, described in the above given patents and papers, used in the reaction of aniline with nitrobenzene it becomes clear that the alkali hydroxides give low yields of the 4-ADFA intermediates. The yields increase substantially when alkali hydroxides are used together with crown ethers. Nevertheless, taking into account their technically demanding preparation, their industrial utilization is not very probable. Also the reaction in the presence of potassium butoxide and in the presence of DMSO shows low selectivity. Contrary to this, if quaternary ammonium hydroxides are used as bases in the reaction, both high selectivity and high yields are achieved. Nevertheless, they have a disadvantage of lower stability, they decompose in a concentrated state and, therefore, they must be stored in diluted aqueous solutions only. An another disadvantage is also their low thermal stability, they easily decompose at higher temperatures [A. Cope et al., Org. reactions, Vol. XI, p. 317, 1960; Hellman H., Angew. Chem. 65, 473–485,1953; F. Moller, Methoden der Organischen Chemie, Houben-Weyl XI/1, p.961–967, 262,1957, and XI/2, p.623, 631–640,1958].

In consequence of the effect of quaternary ammonium hydroxides on primary amines also their alkylation takes place easily. For example, tetramethylammonium hydroxide (TMAH) reacts with aniline, yielding N-methylaniline in an amount which depends on the reaction conditions chosen (U.S. Pat. No. 5,687,691). The N-methylaniline formed can hardly be separated from aniline, but this must be done before recycling aniline back to a further reaction cycle, so that no undesirable methylated derivatives of 4-ADFA arise as admixtures.

A disadvantage of quaternary ammonium hydroxides per se is also their technically demanding manufacture and their high price. Therefore, it is necessary in each cycle to isolate and recycle quaternary ammonium bases for the next production cycle what cannot be performed without lowering their activity.

The object of the present invention is to provide a solution which will utilize the advantages of known solutions, and will eliminate their disadvantages.

DISCLOSURE OF INVENTION

Nature of the present invention consists in a method of preparation of 4-aminodiphenylamine through an intermediate preparation of 4-nitrodiphenylamine and/or 4-nitrosodiphenylamine and/or their salts by the reaction of aniline with nitrobenzene in a liquid medium at a temperature of 50 to 130° C., under normal or reduced pressure, in an inert atmosphere or in the presence of air oxygen, with subsequent hydrogenation of the intermediate of 4-nitrodiphenylamine and/or nitrosodiphenylamine and side products, and by isolation of 4-aminodiphenylamine and side products and recirculation of unconverted raw materials. The nature of the invention consists in that the reaction of aniline with nitrobenzene is performed in a reaction system, consisting of a true zwitterion salt solution with hydroxides of a general formula $$HO^-/(R^1R^2R^3)N^+—CHR^4—(CH_2)_x—Y^-/Z^+$$

where $R^1$ and $R^2$ means methyl to dodecyl,
$R^3$ means methyl, ethyl, phenyl, benzyl,
$R^4$ means hydrogen or methyl
x means an integer of 0 to 5,
$Y^-$ means $CO_2^-$, $SO_3^-$ and
$Z^+$ means a cation of an alkali metal Na, K, Cs or a tetrasubstituted quaternary ammonium cation, like tetramethylammonium, or their mutual combinations, wherein the amounts of both the zwitterion salt and hydroxide are at least equimolar amounts related to the amount of nitrobenzene taken up in the reaction wherein 4-nitrosodiphenylamine and/or 4-nitrodiphenylamine arise, which yield after hydrogenation 4-ADFA, and after the reaction at least a half of the reaction system is recycled.

It has been found that it is preferable to perform the reaction in the presence of a true zwitterion salt solution with hydroxides of the general formula, where $R^1$, $R^2$ and $R^3$ is methyl, $R^4$ is hydrogen, x is 0, $Y^-$ is $CO_2^-$, and $Z^+$ is the potassium cation and/or a tetrasubstituted quaternary ammonium cation, and more preferably, $Z^+$ represents the potassium cation and/or tetraalkylammonium cation having the number of carbons in the alkyl of 1 to 4.

The reaction medium can be formed separately and/or it will be formed in situ in the reaction system from the starting raw materials. The liquid medium for the reaction of aniline with nitrobenzene is formed by water and/or at least one organic compound, chosen from among aniline, pyridine, toluene, xylene, cyclohexane and aliphatic alcohols having the number of carbons in the molecule of 1 to 4.

An advantage of the present method consists mainly in that the reaction system according to this invention, used for the reaction, is technically more easily accessible and more stable than quaternary ammonium hydroxides and quaternary alkyldiammonium hydroxides themselves, while the reaction of aniline with nitrobenzene stays sufficiently selective for forming 4-ADFA intermediates (with a selectivity of at least 50% of 4-nitrodiphenylamine and nitrosodiphenylamine), and the resulting product is obtained with high yields.

One of the advantages of the process according to this invention is also technically accessible wide variety of bipolar to polypolar organic compounds, containing at least one nitrogen cation in their molecules, as well as their stability, not only thermal stability, but also stability under the hydrogenation conditions, and the fact that the reaction system can be regenerated.

It is known from the literature [M. Rabinowitz et al., Angew. Chem. 98, 958–968, 1986] that many organic reactions which are initiated by hydroxides take places under the conditions of the PTC/OH⁻ system, i.e. in the presence of phase transfer catalysts. Commonly used PTC are quaternary ammonium ions.

It is known as well that zwitterion salts have been used in several reactions as phase transfer catalysts, but in this case the assumed mechanism of the effect is different, because from the bipolar inner salt of the true zwitterion and hydroxide a bis-ionic pair arises [Starks, C. et al., Phase Transfer Catalysts Principles and Technique, N. Y. Acad. Press 1978, p. 67, 127, 365; Yu. Sh. Goldberg et al., Dokl. Akad. Nauk SSSR 294, 1387–1391, 1987; Yu. Sh. Goldberg et al., Zhur. Org. Khim. 23, 1561–1563, 1987; Yu. Sh. Goldberg et al., Tetrahedron 46, 1911–1922, 1990].

We designate as true zwitterions such compounds which contain in their molecule besides a carboxylic group also a perlakylated amino group, and these groups form mutually inner salts. These compounds do not contain any movable hydrogen, and they contain a quaternary ammonium group.

In the procedures, known from the literature, the zwitterion salts are used as phase transfer catalysts in a catalytic amount, namely in the amount of 1 to 5 mole %. Now it has been found that in the case of using the method of 4-ADFA intermediates preparation according to the present invention it is possible to achieve full conversion of nitrobenzene with aniline if the reaction is performed with at least equimolar amount of the zwitterion salt and hydroxide related to the amount of nitrobenzene, introduced to the reaction, thus indicating that the course of the reaction is different.

Zwitterion salts, known also as betaines or, eventually, sulfobetaines, are commercially available in the form of intramolecular salts or hydrated forms, or it is possible to prepare them according to procedures, known from the literature [Methoden der organischen Chemie (Houben-Weyl), X(12, p. 627–630, 1958; Ullmans Enzyklopädie der technischen Chemie, Vol. 2, p. 497–498, Verlag Chemie 1982; Goldberg Yu. Sh. et al., Tetrahedron 46, 1911–1922, 1990; Goldberg Yu. Sh. et al., Dokl. Akad. Nauk SSSR 297, 1387–1391, 1987; Willstätter R., Ber. 35, 584–620–1907, U.S. Pat. No. 4,672,077 and Belg. patent 903 785].

In preparing the reaction system for condensation of aniline with nitrobenzene it is possible to proceed in such a way that a solution of hydroxide in a protic solvent (in water, in methanol or in 2-propanol) is prepared, and crystalline zwitterionic salt, possibly in the form of a hydrate, is added, and the corresponding solvent, for example aniline, is added to it. One can proceed also in such a way that aniline is added to a hydroxide solution in a protic solvent, and zwitterionic salt is added to this mixture. If preparing a reaction system, consisting of a mixture of hydroxides, one may proceed also in such a way that to a diluted aqueous solution of quaternary ammonium hydroxide crystalline zwitterionic salt is added, and after its dissolving solid alkali hydroxide, and finally aniline is added. It is also possible to prepare a methoxide solution by dissolving an alkali metal, its oxide or hydroxide in methanol, and adding a solution of the zwitterionic salt in aniline.

It is possible to vary the mutual ratios of the reaction components in a wide range in such a way, that the limiting component is either the zwitterion salt or nitrobenzene or aniline. Their mutual ratios may be chosen in such a way that the reaction will take place in an optimum, technologically and economically acceptable process.

The reaction may be performed in a wide range of temperatures from 50° C. to 130° C., depending on the reaction system used.

The reaction may be further performed in an inert atmosphere or under aerobic conditions, at the atmospheric pressure or at a reduced pressure, while the yield, conversion and selectivity of the reaction depend on the conditions chosen.

Further auxiliary protic and aprotic solvents may be used in the reaction, like tertiary butylalcohol, DMSO, diethyleneglycol dimethylether, ethyleneglycol monomethylether, toluene, xylene, cyclohexane, and so on.

The main products, obtained by the reaction, are 4-NODFA and 4-NO$_2$DFA which are present in the reaction mixture in a free form or in the form of salts. Besides them and reaction water the reaction mixture may contain further substances, like 4-phenylazodiphenylamine, azobenzene, azoxybenzene, 2-nitrodiphenylamine, phenazine or phenazine oxide, depending on the choice of molar ratios of the reaction components of the system, as well as on the chosen type of zwitterions, their salts, on the protic solvent, possibly on the auxiliary solvent and their concentration in the reaction mixture, on temperature, reaction time and conversion degree of nitrobenzene. These facts are well known to experts in this field.

4-ADFA is obtained from the mixture of 4-NODFA, 4-NO$_2$DFA and 4-phenylazodiphenylamine or their salts so, that the reaction mixture is after diluting by a solvent subjected to catalytic hydrogenation by known procedures.

EXAMPLES OF EMBODIMENTS

Following examples illustrate, but do not limit the scope of claims in any way.

Example 1

Results of the Reaction of Aniline with Nitrobenzene Under Anaerobic Conditions, when the Reaction System is a Solution of Betaine and Potassium Hydroxide in Methanol at Different Temperatures in the Range of 55 to 130° C.

For the reaction an apparatus was used which consisted of a 100 ml 3-neck flask with a magnetic stirrer, a thermometer, a dropping funnel and an azeotropic attachment, and was joined with a water-jet pump.

3,5 g (84.02%) of potassium hydroxide (0.052 mol) were dissolved in 6 g of methanol. 6.1 g of betaine (0.052 mol) were added and, after heating up to 50° C., 37.0 g of aniline (0.49 mol) were added. Air in the apparatus was replaced by nitrogen and after heating up to the reaction temperature at first methanol was distilled off at a pressure of 5.2 kPa, and then nitrobenzene, 6.4 g (0.052 mol) on the whole, was dosed under intensive stirring during 1.5 h. The reaction mixture was left to react for further 3 hours, then it was cooled down, diluted by methanol, and analyzed by the method of highly effective liquid chromatography. The yield of reaction components was calculated relative to the amount of nitrobenzene, introduced into the reaction. Further reaction conditions and results achieved are given in Table 1.

TABLE 1

| | Yield, related to the introduced nitrobenzene (%) | | | |
|---|---|---|---|---|
| Temperature (° C.) | 4-NODFA | 4-NO$_2$DFA | Azobenzene | Phenazine |
| 55 | 18.2 | 10.0 | 8.5 | — |
| 70 | 33.3 | 18.7 | 7.3 | 1.4 |
| 90 | 40.3 | 23.1 | 28.0 | 2.9 |
| 130 | 22.2 | 22.2 | 44.1 | 9.3 |

Example 2

Results of the Reaction of Aniline with Nitrobenzene, when Using Lithium, sodium, Potassium and Cesium Hydroxide in a Reaction System, Containing Betaine-hydroxide.

The reaction systems were prepared by the reaction of betaine monohydrate with alkali hydroxides. According to the procedure, described in Example 1, 3 identical reactions were performed at a temperature of 70° C. with various cations of alkali metals, given in Table 2.

| | Yield of the reaction in % of the charged nitrobenzene | | | |
|---|---|---|---|---|
| Cation | 4-NODFA | 4-NO$_2$DFA | Azobenzene | Phenazine |
| Li$^+$ | 0.15 | 0.34 | 0.24 | — |
| Na$^+$ | 24.7 | 31.1 | 31.6 | 10.9 |
| K$^+$ | 36.0 | 16.3 | 13.8 | — |
| Cs$^+$ | 39.1 | 17.6 | 10.8 | 9.8 |

Example 3

Results of the Reaction of Aniline with Nitrobenzene with the Reaction System Betaine-sodium Hydroxide in Methanol Under Aerobic Conditions.

To a catalyst solution, consisting of 0.066 mol of betaine and 0.066 mol of sodium hydroxide in 15 g of methanol, 0.4 mol of aniline were added. After heating the reaction mixture up to 70° C. nitrobenzene was dosed to the reaction mixture in the course of 1.5 h. Methanol and reaction water were gradually removed from the reaction mixture at a reduced pressure. After completing the nitrobenzene dosing the mixture was stirred for further 3.5 h. After dilution by methanol the mixture was analyzed, and the yield of the reaction products, expressed in %, related to nitrobenzene, charged to the reaction mixture, has achieved:

4-NODFA 26.3%; 4-NO$_2$DFA 16.8%; 4-FADFA 5.1%; azobenzene 40.8%.

Example 4

Modified Procedure in which all Reaction Components were Introduced into the Reaction at the Beginning.

In a flask, 2.66 g (83.0%) of potassium hydroxide were dissolved in 5.0 ml of water, 5.31 g of betaine hydrate, 24.1 g of aniline and 4.83 g of nitrobenzene were added. The reaction mixture was intensively stirred at 80° C. in nitrogen atmosphere for 5 h. Within this time interval pressure in the apparatus was gradually reduced from 53 kPa down to 2.6 kPa. Finally, the reaction mixture was dissolved in methanol and analyzed by the method of highly effective liquid chromatography. Conversion of nitrobenzene was 75.6%, and the yields (in %) of individual products, calculated relative to the introduced nitrobenzene, were as follows:

4-NODFA 35.7%; 4-NO$_2$DFA 17.8%; 4-FADFA 0.12%; azobenzene 10.9%; phenazine 1.25%.

Example 5

Reaction of Aniline with an Excess of Nitrobenzene (as a solvent) in the Presence of the Reaction System Betaine-potassium Hydroxide Under Anaerobic Conditions.

To a solution of 3.38 g (83%) of potassium hydroxide in 3.0 ml of water 6.85 g of betaine hydrate and 26.8 g of nitrobenzene were added. At a temperature of 80° C. and at a pressure of 20 kPa 4.9 g of aniline were dosed to the reaction mixture in nitrogen atmosphere during 1.5 h. After completing the nitrobenzene dosing the reaction mixture was intensively stirred for further 6 h. After cooling down the reaction mixture was dissolved in methanol. The yields, calculated as related to aniline, charged to the reaction, have achieved:

4-NODFA 1.5%; 4-NO$_2$DFA 0.2%; azobenzene 2.5%.

Example 6

Effect of the Molar ratio Betaine-potassium Hydroxide to Nitrobenzene on the Course of the Reaction.

By the procedure, given in Example 1, reactions of aniline with nitrobenzene with the molar ratio of 7:1 were performed with the difference that the molar ratio of the reaction System to nitrobenzene was changing from 1:1 to 1.5:1. The reaction system was formed by betaine hydrate and potassium hydroxide with the molar ratio of 1:1 in a methanol solution. Results of the experiments, given in Table 3, have shown the effect of the increasing amount of the reaction system on the yields of the reaction and conversion of nitrobenzene.

TABLE 3

| Molar ratio of catalyst to nitrobenzene | Conversion of nitrobenzene | Yield, calculated in relation to the introduced nitrobenzene (%) | | | | |
|---|---|---|---|---|---|---|
| | | 4-NODFA | 4-NO$_2$DFA | 4-FADFA | AB | Phenazine |
| 1.1:1 | 89.1 | 58.6 | 14.6 | 0.2 | 17.0 | 1.3 |
| 1.2:1 | 91.6 | 63.0 | 14.1 | 0.2 | 14.6 | 1.1 |
| 1.3:1 | 93.6 | 66.1 | 12.9 | 0.2 | 13.9 | 1.6 |
| 1.5:1 | 95.6 | 71.5 | 12.8 | 0.3 | 13.2 | 2.5 |

Note: The abbreviation AB in the table means azobenzene

Example 7

Reaction of Aniline with Nitrobenzene Under the Conditions, where Water (reaction water and water, introduced as a solvent) is Continually Removed from the Reaction Medium, Particularly by Distillation in the Form of an Azeotrope Water-aniline, while Vacuum in the System is Gradually Decreased.

114.0 g (0.131 mol) of 20% solution of an equimolar amount of betaine and potassium hydroxide were introduced into a 500 ml three-neck flask, and after heating up to 50° C. water was distilled off under vacuum, until crystalline slurry remained in the flask.

72.3 g of aniline (0.776 mol) were added, and 13.5 g (0.1097 mol) of nitrobenzene were dosed to the reaction mixture during 1.5 h at 80° C. in nitrogen atmosphere under intensive stirring. In the course of aniline adding a pressure of 26 kPa was maintained in the flask, while an azeotrope water-aniline distilled. During the final stage of the reaction in which the reaction mixture was stirred for further 4.5 h, the pressure in the apparatus was gradually reduced from the starting 26 kPa down to 4 kPa at the end of the reaction. After cooling down the reaction mixture was analyzed. A 100% conversion of nitrobenzene was achieved with the following yields (in %) of individual reaction components (calculated in relation to the introduced nitrobenzene):

4-NODFA 82.1%; 4-NO$_2$DFA 11.7%; azobenzene 11.6%; phenazine 1.4%.

Example 8

Reaction of Aniline with Nitrobenzene in the Presence of a Reaction System which was Aqueous Solution of N,N,N-trisubstituted Ammonio-alkyl Carboxylate of the Formula.

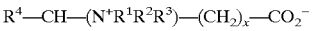

(where R$^1$, R$^2$, R$^3$, R$^4$ and the Parameter x are Given in the Table) and Potassium Hydroxide in an Aqueous Solution.

0.26 mol of aniline were added to a mixture, prepared of 0.04 mol of the corresponding substituted betaine monohydrate, 0.04 mol of potassium hydroxide (86.0%) and of 5 ml of water. 0.039 mol of nitrobenzene on the whole were dosed to the reaction mixture during 1.5 h at 80° C. and at a pressure of 14 kPa under the protecting nitrogen atmosphere. The reaction mixture was stirred for further 4 h to finish the reaction. Conversion of the reaction and the yield of 4-ADFA intermediates (i.e. 4-NODFA, 4-NO$_2$DFA and 4-FADFA), calculated in relation to the reacted nitrobenzene, were determined (Table 4).

TABLE 4

| Values of parameters | | | | | | |
|---|---|---|---|---|---|---|
| $R^1$ | $R^2$ | $R^3$ | $R^4$ | x | Conversion (%) | Yield (%) |
| $C_6H_5$ | $CH_3$ | $CH_3$ | H | 0 | 42.3 | 11.2 |
| n-$C_{12}H_{25}$ | $CH_3$ | $CH_3$ | H | 0 | 58.0 | 31.7 |
| n-$C_8H_{17}$ | $CH_3$ | $CH_3$ | H | 0 | 87.2 | 50.0 |
| $C_6H_5$—$CH_2$ | $CH_3$ | $CH_3$ | H | 0 | 36.2 | 32.7 |
| $CH_3$ | $CH_3$ | $CH_3$ | H | 1 | 62.2 | 61.0 |
| $C_2H_5$ | $C_2H_5$ | $C_2H_5$ | H | 0 | 55.8 | 52.1 |
| $CH_3$ | $CH_3$ | $CH_3$ | H | 5 | 60.4 | 48.3 |
| $CH_3$ | $CH_3$ | $CH_3$ | $CH_3$ | 0 | 35.2 | 25.8 |

Example 9

Reaction of Aniline with Nitrobenzene in the Presence of the Reaction System Betaine-potassium Hydroxide in Methanol Under Anaerobic Conditions.

48.2 g of aniline (7-fold molar excess, related to nitrobenzene) were added to a solution of 5.8 g of potassium hydroxide and 11.9 g of betaine hydrate (10% molar excess, related to nitrobenzene), and the reaction mixture was heated up to 75° C., air in the apparatus was replaced by nitrogen, and nitrobenzene was dosed under intensive stirring at a starting pressure of 26 kPa during 2 h. The reaction was continuing for further 3 h, while pressure was gradually reduced down to 6 kPa. The reaction was terminated by cooling down and dissolving the reaction mixture in methanol. 96.7% conversion of nitrobenzene and following yields (in %), related to the introduced nitrobenzene, were achieved:

4-ADFA intermediates 80.5%; azobenzene 11.0%; phenazine 4.2%.

Example 10

Reaction of Aniline with Nitrobenzene in the Presence of a Reaction System of Trimethylammonio-propane Sulfonate and Potassium Hydroxide in an Aqueous Solution.

0.517 mol of aniline were added at 80° C. to a solution of a catalyst, consisting of 0.0858 mol of trimethylammonio-propane sulfonate and 0.0858 mol of potassium Hydroxide in 6.6 ml of water. A part of water was distilled off at a reduced pressure (21 kPa) as azeotrope, then nitrobenzene was dosed into the reaction mixture under intensive stirring at 80° C. and a pressure of 26 kPa during 1.5 h. A viscous mixture arose which was stirred for further 3 hours. Then it was diluted by methanol, and it was analyzed. Nitrobenzene conversion reached 71.1%. The yield of the reaction products, related to nitrobenzene, charged to the reaction, has achieved (in %):

4-ADFA intermediates 28.6%; azobenzene 7.2%; phenazine 0.5%.

Example 11

Influence of Auxiliary Polar Solvents on the Reaction of Aniline with Nitrobenzene in the Presence of a Reaction System of Betaine and Potassium Hydroxide.

48.0 g of aniline were added to a prepared aqueous solution of betaine and potassium hydroxide with a molar ratio of 1.2 mol to 1 mol of nitrobenzene, and the excess water was distilled off at a reduced pressure. Then 15 ml of an auxiliary solvent were added, and nitrobenzene was added under intensive stirring in an inert atmosphere at 70° C., and at a reduced pressure (7 kPa) during 1.5 h. After further 2 hours the reaction was interrupted, the overall reaction time being 3.5 h. The results are given in Table 5.

TABLE 5

| Auxiliary solvent | Nitrobenzene conversion, % | Yield of 4-ADFA intermediates |
|---|---|---|
| — | 41.1 | 36.5 |
| DMSO | 79.0 | 65.9 |
| Polyethylene glycol 350 | 72.7 | 34.4 |
| Dimethyl formamide | 11.3 | 2.8 |
| Diethyleneglycol dimethylether | 72.2 | 34.4 |

Example 12

Influence of a Crown Ether as the Phase Transfer Agent on the Conversion and Yield of the Reaction.

Experimental Conditions:

Mole ratio of aniline: nitrobenzene: betaine-KOH: 18 dibenzocrown-6-ether=7:1:1.1:0.1; the reaction took place in an inert atmosphere at 80° C. and at a pressure of 7.3 kPa during the overall reaction time of 6 h (Table 6).

TABLE 6

| Molar amount of crown ether | Nitrobenzene conversion, % | Yield, related to the charged nitrobenzene, % | | | |
|---|---|---|---|---|---|
| | | NODFA | 4-NO$_2$DFA | azobenzene | phenazine |
| 0 | 92.8 | 65.0 | 14.9 | 16.3 | 1.3 |
| 0.1 | 97.7 | 68.3 | 13.2 | 15.7 | 2.1 |

Example 13

A procedure was Tested at Which a Solution of Betaine and Potassium Hydroxide was Dosed into the Reaction Mixture of Reagents Under Aerobic Conditions.

A solution, consisting of 6.0 g of potassium hydroxide (KOH concentration of 84%), 12.1 g of betaine and 10.5 ml of water, was dosed into a mixture of 9.6 g of nitrobenzene and 48.0 g of aniline under intensive stirring at 80° C. and a pressure of 8 kPa during 2 h. Stirring continued further 2 h and 45 minutes under azeotrope distillation. After cooling down the reaction mixture was dissolved in methanol, and it was analyzed. With 94.7% nitrobenzene conversion following yields (in %), related to nitrobenzene, introduced into the reaction, were achieved:

4-ADFA intermediates 76.6%; azobenzene 16.9%; phenazine 1.2%.

Content of M-methylaniline was less than 0.05% (related to the introduced betaine).

Example 14

Reaction of Aniline with Nitrobenzene in the Presence of a Reaction System According to this Invention Under Normal Pressure, without Distilling off the Solvent from the Reaction Mixture Under Anaerobic Conditions.

Nitrobenzene (4.7 g) was dosed into a reaction mixture, consisting of 24.0 g of aniline, 2.68 g of 84% potassium hydroxide, 5.5 g of betaine hydrate and 3 g of methanol, at 75° C. and normal pressure in nitrogen atmosphere during 2 h. Then the reaction mixture was stirred for further 2 hours at 80° C. under reflux. After cooling down and diluting with methanol the mixture was analyzed. Nitrobenzene conversion achieved 75.1%. The yields (in %), related to the introduced nitrobenzene:

4-ADFA intermediates 57.0%; azobenzene 5.5%; phenazine 1.8%.

Example 15
Influence of Polarity of Auxiliary Solvents, Forming Azeotropic Mixtures with Water, on the Course of the Reaction of Nitrobenzene with Aniline Under Anaerobic Conditions.

0.078 mol of nitrobenzene were dosed into a reaction mixture, consisting of 0.09 mol of KOH (84.0% concentration), 0.09 mol of betaine hydrate, 4 ml of water, 0.51 mol of aniline and 15 ml of an auxiliary solvent, at 80° C. during 1.5 h. Completing the reaction required further 4.5 h, while water was continuously removed from the reaction medium as an azeotrope with the auxiliary solvent. In an experiment with 2-propanol, the azeotrope was distilled off through a short column under an atmospheric pressure. In an experiment with pyridine, the azeotrope distilled at a reduced pressure of 13.3 to 9.3 kPa. In an experiment with cyclohexane water was continuously removed as an azeotrope by means of an azeotropic attachment. The results are given in the following Table 7.

TABLE 7

| Auxiliary solvent | Nitrobenzene conversion, % | Yield, related to charged nitrobenzene, % | | | |
|---|---|---|---|---|---|
| | | NODFA | 4-NO$_2$DFA | azobenzene | phenazine |
| 2-propanol | 95.5 | 65.8 | 7.1 | 17.2 | 1.3 |
| pyridine | 100 | 62.2 | 21.9 | 14.0 | 1.9 |
| cyclohexane | 88.1 | 53.0 | 24.0 | 11.4 | 1.0 |

Example 16

Reaction of Aniline with Nitrobenzene by the Effect of a Reaction System, Consisting of an Aqueous Solution of Betaine and Potassium Hydroxide with Various Mutual Molar Ratios and at Various Ratios to Nitrobenzene.

The reaction procedure is analogous to that of Example 8. Mutual molar ratios of betaine and KOH to 1 mol of nitrobenzene and the results achieved are given in Table 8.

TABLE 8

| Molar amount of KOH | Molar amount of betaine | Nitrobenzene conversion, % | Yield of 4-ADFA intermediates, % |
|---|---|---|---|
| 0.22 | 0.22 | 21.8 | 20.7 |
| 0.6 | 0.6 | 53.4 | 48.1 |
| 0.8 | 1.0 | 82.0 | 73.7 |
| 1.0 | 0.2 | 34.8 | 12.1 |
| 1.0*** | — | 9.1 | 2.3 |

***A comparative example, it does not correspond to this invention

Example 17
Effect of Water Content on the Reaction of Aniline with Nitrobenzene.

A reaction mixture, consisting of aniline, nitrobenzene, potassium hydroxide, betaine and water with mutual molar ratios, given in Table 9, was let to react under intensive stirring at 80° C. at an atmospheric pressure under nitrogen during 6 h. After cooling down and diluting with methanol the obtained solution was analyzed, and the results were expressed in nitrobenzene conversion and yields, related to the charged nitrobenzene. Water in the reaction mixture is a sum of the reaction water, dissolving water and water, introduced by raw material, and it is expressed in mol per 1 mol of nitrobenzene.

TABLE 9

| Mole ratios if input raw materials | | | | | Yields, related to charged nitrobenzene, % | | | |
|---|---|---|---|---|---|---|---|---|
| NB | Betaine-KOH | Water | Aniline | NB conversion, % | NODFA | NO$_2$DFA | AB | PHEN |
| 1 | 1.2 | 2.05 | 7 | 85.0 | 46.0 | 21.9 | 24.9 | 0.7 |
| 1 | 1.2 | 4.25 | 7 | 61.2 | 51.7 | 8.8 | 11.5 | 0.9 |
| 1 | 1.2 | 8.8 | 7 | 1.4 | 0.6 | 0.5 | 0.1 | — |

Symbol meanings in the table:
NB - nitrobenzene;
AB - azobenzene;
PHEN - phenazine

Example 18

Influence of different molar ratios of organic and inorganic hydroxides to betaine on the condensation of aniline with nitrobenzene and, simultaneously, influence of betaine and tetramethylammonium hydroxide (TMAH) on aniline methylation to N-methylaniline (N-MAn) is obvious from the results in Table 10.

Seven-fold molar excess of aniline was added to a prepared aqueous solution of individual components of the reaction system, consisting of TMAH, betaine and potassium hydroxide. After azeotropic distilling off the water, 0.95 mol of nitrobenzene were added to the reaction mixture at 70° C. and at a pressure of 7.3 kPa during 1.5 h. The reaction was completed after further 2 h. Yield (Table 10) of the components in the reaction product has been calculated in relation to the introduced nitrobenzene. N-methylaniline (N-MAn) was expressed in mole per cent, related to the introduced TMAH.

TABLE 10

| Molar amounts of substances, mol | | | Reaction temperature, | Yields, related to the introduced nitrobenzene, % | | | | N-MAn |
|---|---|---|---|---|---|---|---|---|
| TMAH | KOH | Betaine | ° C. | NODFA | NO$_2$DFA | AB | PHEN | % |
| 1 | — | 1 | 75 | 86.9 | 8.5 | 3.7 | 0.7 | <0.05 |
| 1* | — | — | 75 | 87.9 | 6.9 | 6.0 | 1.0 | 1.0 |
| 0.3 | 0.7 | 1 | 75 | 76.9 | 17.2 | 6.5 | 1.1 | <0.05 |
| 0.5 | 0.5 | 1 | 75 | 56.9 | 8.1 | 1.0 | 0.13 | <0.05 |
| —** | 1.15 | 1.15 | 75 | 64.6 | 14.3 | 12.2 | 1.33 | <0.05 |

*A comparative example, it does not correspond to this invention

Determinability limit for M-NAn with the method used is 0.05%.

Example 19

Reaction mixture, obtained by the procedure of Example 7, was diluted by addition of 30% by weight of methanol, the catalyst Raney Ni was added in an amount of 30% by weight in water (related to the amount of nitrobenzene, charged to the reaction). The reaction took place at 60° C. and at a starting pressure of 5 MPa for 7 minutes. A sample of the reaction mixture, taken away, was analyzed for content of 4-ADFA. The overall yield, related to the starting content of 4-NODFA, 4-NO$_2$DFA and 4-FADFA, was 99.1%. The yield of 4-ADFA, related to the reacted nitrobenzene, was 88.5%.

Example 20
Batch Solution of the Reaction with Subsequent Processing of the Condensation Mixture, and Isolation of the 4-ADFA Product.

For the reaction of aniline with nitrobenzene by the action of the reaction system of a solution of trimethylammonioacetate with potassium hydroxide a device was used, consisting of a reactor with a volume of 250 l, provided with a rapid agitator, a tempering jacket which was heated by warm water to regulate the temperature in the reactor, a nitrogen inlet under the surface of the reaction mixture, a condensator for condensation of vapours from the reactor, and a receiver for condensate collection which was used as a phase separator, and it was provided with an overflow for recycling the aniline phase with a content of nitrobenzene back to the reactor, while the separated aqueous phase of the condensate was permanently removed from the phase separator. The reactor was further provided with a thermometer and a pressure regulator.

19.1 l of distilled water, 12.8 kg of solid KOH, containing 86.5% of KOH, were inserted into an auxiliary vessel having the volume of 50 l, and after it had dissolved, 26.6 kg of betaine hydrate were added. After dissolving of all components the reaction system in the form of an aqueous solution was prepared to be used in the reaction.

111.8 kg (1.2 kmol) of aniline were inserted into the reactor, and 58.5 kg of the above given solution were added. The reactor was closed and was purged by nitrogen once, while the mixture was stirred. After termination of the reactor purging by nitrogen an absolute pressure of 20 kPa was set in the reactor, and the reactor content was gradually heated up to a temperature of 80° C. After reaching the temperature 21.1 kg of nitrobenzene (0.17 kmol) were started to be dosed into the reactor at such a rate that all nitrobenzene was fed within 1.5 h. The azeotrope aniline-water which was distilled off the reactor was collected in the receiver, where aqueous and aniline phase were separated. The aniline phase contained a certain amount of nitrobenzene and, therefore, it was periodically recycled to the condensation reactor during the whole experiment. After completing the dosing of nitrobenzene pressure in the reactor was gradually reduced to a value of 14 kPa, and the reaction mixture reacted at this pressure and at a temperature of 80° C. for 1.5 h. Then the pressure was gradually reduced to 8 kPa, and at this pressure the reaction mixture reacted for 1.5 h. Finally, pressure in the reactor was reduced to the value 4 kPa, and the reaction mixture was let to complete the reaction within 1.5 h. Finally it was cooled down to 40° C., approximately 15% of methanol were added, it was discharged from the reactor and weighed. An analysis of the reaction mixture has shown that 100% conversion of nitrobenzene took place with the following yield (in %) of individual reaction components (calculated in relation to the introduced nitrobenzene):

4-NODFA 77.0%; 4-NO$_2$DFA 14.3%; 4-phenylazodiphenylamine 0.21%; azobenzene 9.6%; phenazine 1.3%.

Note: Content of N-methylaniline was less than 0.05%, related to the introduced betaine.

Reaction mixture from the condensation was diluted by methanol in such a way that its content in the diluted condensation mixture was 30% by weight, and it was hydrogenated under conditions, given in Example 19. A withdrawn sample of the reaction mixture was analyzed for the content of 4-ADFA. The overall yield of 4-ADFA, related to the starting content of 4-NODFA, 4-NO$_2$DFA and 4-FADFA, was 99.2%. The yield of 4-ADFA in the hydrogenate, related to the nitrobenzene reacted, was 89.9%.

After completing the hydrogenation the catalyst Raney Ni was filterred off, and it was washed by methanol and distilled water. The washing solutions were added to the hydrogenate. Methanol was distilled off the diluted hydrogenate at an absolute pressure of 35 kPa and at a temperature of 60 to 70° C. After distilling off methanol the hydrogenate was separated to aqueous and organic phase, while the organic phase was after separation again extracted by distilled water, and the phases were subsequently separated. To facilitate the phase separation a small amount of toluene was added to the organic phase. The organic phase residues in the aqueous phase were removed by extraction with toluene which was subsequently added to the organic phase.

The aqueous phase, treated in this way, constituted a reaction system which was used in the following experiment (Example 21).

Aniline and a small part of forerun were distilled off the organic phase of the hydrogenate at a pressure of 2 to 3 kPa and at a temperature of 70 to 180° C. The rest in the cooker consisted of raw 4-ADFA with a content of 1.6% by weight of phenazine which was then rectified on an effective vacuum column. Distilled 4-ADFA, containing 99.3% of active substance, was obtained, while the yield of the distilled 4-ADFA, related to the reacted nitrobenzene, was 86.4%.

That part of nitrobenzene which reacted in the condensation to azobenzene was hydrogenated to aniline. This has manifested itself in favourable balance of the recycled aniline in the course of the 4-ADFA preparation procedure (condensation, hydrogenation, rectification of 4-ADFA), where more aniline was regenerated than corresponding to its consumption for 4-ADFA formation.

Example 21
Using a Recycled Reaction System in the Condensation.

Method of condensation of aniline with nitrobenzene was as in Example 20, while a recycled reaction system was inserted into the reactor to aniline, i.e. the corresponding amount of processed aqueous phase from the hydrogenation (Example 20), so that the molar ratio catalyst: nitrobenzene was 1.15.

After accomplishing the condensation a sample was withdrawn from the condensation reaction mixture. According to analysis the nitrobenzene conversion was 95.5% with subsequent yield (in %) of individual reaction components (related to the introduced nitrobenzene):

4-NODFA 73.5%; 4-NO$_2$DFA 13.5%; 4-phenylazodiphenylamine 0.17%; azobenzene 12.6%; phenazine 1.2%.

Note: Content of N-methylaniline was less than 0.05%, related to the introduced betaine.

What is claimed is:

1. Method of preparation of 4-aminodiphenylamine through an intermediate preparation of 4-nitrodiphenylamine and/or 4-nitrosodiphenylamine and/or their salts by the reaction of aniline with nitrobenzene in a liquid medium at a temperature of 50 to 130° C., under normal or reduced pressure, in an inert atmosphere or in the presence of air oxygen, with subsequent hydrogenation of the intermediate of 4-nitrodiphenylamine or 4-nitrosodiphenylamine and side products, and by isolation of 4-aminodiphenylamine and the side products and recirculation of unconverted raw materials, characterized in that the reaction of aniline with nitrobenzene is performed in a reaction system, consisting of a solution of salts of true zwitterions with hydroxides of a general formula $$HO^-(R^1R^2R^3)N^+\text{—}CHR^4\text{—}(CH_2)_x\text{—}Y/Z^+$$

where
R$^1$ and R$^2$ means methyl, ethyl, or C$^3$–C$^{12}$ linear alkyl group,
R$^3$ means methyl, ethyl, phenyl, benzyl,
R$^4$ means hydrogen or methyl,
x means an integer of 0 to 5,
Y$^-$ means CO$_2^-$, SO$_3^-$ and
Z$^+$ means a cation of an alkali metal Na, K, Cs, or a tetrasubstituted quaternary ammonium cation, or their mutual combination, wherein the amounts of both the zwitterion salt and hydroxide are at last equimolar amounts related to the amount of nitrobenzene taken up in the reaction wherein 4-nitrosodiphenylamine and/or 4-nitrodiphenylamine arise, which yield after hydrogenation 4-AFDA, and after the reaction at least a half of the reaction system is recycled.

2. Method according to claim 1, characterized in that the reaction is performed in the presence of a solution of salts of true zwitterions with hydroxides of the general formula, where R$^1$, R$^2$ and R$^3$ is methyl, R$^4$ is hydrogen, x is 0, Y$^-$ is CO$_2^-$, and Z$^+$ is at least one from the group consisting of a potassium cation and a tetrasubstituted quaternary ammonium cation.

3. Method according to claim 1 or 2, wherein Z$^+$ represents at least one from the group consisting of potassium cation and tetraalkylammonium cation having between 1–4 carbon atoms in the alkyl.

4. Method according to claim 1 or 2, wherein the reaction medium is formed either separately, or in situ in the reaction system from raw materials.

5. Method according to claim 1 or 2, where the liquid medium for the reaction of aniline with nitrobenzene is formed from the group consisting of: (1) water and (2) at least one organic compound from the group consisting of aniline, pyridine, toluene, cyclohexane, and aliphatic alcohols having between 1–4 carbon atoms in the molecule.

6. A method according to claim 1, wherein Z$^+$ is a tetramethylammonium cation.

7. The method of claim 1, wherein the liquid medium further comprises an auxiliary cosolvent.

8. The method of claim 7, wherein the cosolvent is one or more of tert-butyl alcohol, dimethylsulfoxide, diethyleneglycol, dimethylether, ethyleneglycol, monomethylether, toluene, xylene, or cyclohexane.

9. A method of preparing 4-aminodiphenylamine comprising the steps of:

reacting aniline with nitrobenzene in a liquid medium at a temperature of 50 to 130° C. in the presence of salts of true zwitterions with hydroxides of a general formula:

$$HO^-/(R^1R^2R^3)N^+\text{—}CHR^4\text{—}(CH_2)_x\text{—}Y/Z^+$$

wherein
R$^1$ and R$^2$ is a methyl, ethyl, or C$^3$–C$^{12}$ linear alkyl group,
R$^3$ is methyl, ethyl, phenyl, or benzyl,
R$^4$ is hydrogen or methyl,
x is an integer between 0 to 5,
Y$^-$ is CO$_2^-$ or SO$_3^-$ and
Z$^+$ is one or more of Na, K, Cs, or a tetrasubstituted quaternary ammonium cation, wherein the amount of the zwitterion salt and the hydroxide are at last equimolar to the amount of nitrobenzene consumed in the reaction, and wherein unreacted aniline and nitrobenzene is recirculated to provide a reaction mixture comprising 4-nitrodiphenylamine and/or 4-nitrosodiphenylamine and/or their salts and side products;

hydrogenating the reaction mixture to provide a hydrogenated reaction mixture;

isolating the 4-aminodiphenylamine and the side products from the hydrogenated reaction mixture.

10. The method of claim 9, wherein R$^1$, R$^2$, and R$^3$ is methyl; R$^4$ is hydrogen; x is 0; Y$^-$ is CO$_2^-$; and Z$^+$ comprises at least one of a K cation or a tetrasubstituted ammonium cation.

11. The method of claim 10, wherein Z$^+$ comprises at least one of a K cation or a tetrasubstituted ammonium cation wherein the alkyl groups have between 1 and 4 carbon atoms.

12. The method of claim 9, wherein the reaction medium is formed separately or in situ from the aniline and nitrobenzene.

13. The method of claim 9, wherein the liquid medium comprises water and one or more of aniline, pyridine, toluene, xylene, cyclohexane, or a $C_1$ to $C_4$ aliphatic alcohol.

14. The method of claim 1, wherein $Z^+$ is tetramethylammonium cation.

15. The method of claim 9, wherein the liquid medium further comprises an auxiliary cosolvent.

16. The method of claim 15, wherein the cosolvent is one or more of tert-butyl alcohol, dimethylsulfoxide, diethyleneglycol, dimethylether, ethyleneglycol, monomethylether, toluene, xylene, or cyclohexane.

* * * * *